United States Patent
Li et al.

(10) Patent No.: US 9,084,984 B2
(45) Date of Patent: Jul. 21, 2015

(54) METHOD FOR SELECTIVE HYDROGENATION OF PHENYLACETYLENE IN THE PRESENCE OF STYRENE

(75) Inventors: Siqin Li, Shanghai (CN); Juntao Liu, Shanghai (CN); Fengxia Sun, Shanghai (CN); Wanmin Wang, Shanghai (CN); Yuanlin Cheng, Shanghai (CN)

(73) Assignees: China Petroleum & Chemical Corporation, Beijing (CN); Shanghai Research Institute of Petrochemical Technology, Sinopec, Shanghai (CN)

( * ) Notice: Subject to any disclaimer, the term of this patent is extended or adjusted under 35 U.S.C. 154(b) by 0 days.

(21) Appl. No.: 13/140,616

(22) PCT Filed: Dec. 17, 2009

(86) PCT No.: PCT/CN2009/001486
§ 371 (c)(1), (2), (4) Date: Sep. 6, 2011

(87) PCT Pub. No.: WO2010/069144
PCT Pub. Date: Jun. 24, 2010

(65) Prior Publication Data
US 2011/0308999 A1    Dec. 22, 2011

(30) Foreign Application Priority Data
Dec. 18, 2008 (CN) .......................... 2008 1 0044146

(51) Int. Cl.
| | | |
|---|---|---|
| *C10G 35/09* | (2006.01) | |
| *B01J 29/46* | (2006.01) | |
| *B01J 23/44* | (2006.01) | |
| *B01J 23/755* | (2006.01) | |
| *B01J 23/89* | (2006.01) | |
| *B01J 37/08* | (2006.01) | |
| *C07C 7/167* | (2006.01) | |
| *B01J 21/04* | (2006.01) | |

(52) U.S. Cl.
CPC *B01J 29/46* (2013.01); *B01J 23/44* (2013.01); *B01J 23/755* (2013.01); *B01J 23/892* (2013.01); *B01J 37/084* (2013.01); *C07C 7/167* (2013.01); *B01J 21/04* (2013.01)

(58) Field of Classification Search
CPC ................................ C10G 35/09; B01J 21/18
USPC ................. 585/250–277; 208/141, 142–145; 502/152–157, 161, 174, 180–185
See application file for complete search history.

(56) References Cited

U.S. PATENT DOCUMENTS

| | | | |
|---|---|---|---|
| 4,508,836 A | 4/1985 | Haag et al. | |
| 5,156,816 A | 10/1992 | Butler et al. | |
| 6,239,056 B1 | 5/2001 | Gajda et al. | |
| 6,429,347 B1 | 8/2002 | Boldingh | |
| 6,555,073 B1 * | 4/2003 | Butler et al. | 422/636 |
| 6,635,791 B1 | 10/2003 | Magne-Drisch et al. | |
| 6,747,181 B1 * | 6/2004 | Bosman et al. | 585/259 |
| 7,105,711 B2 | 9/2006 | Merrill | |
| 7,838,710 B2 | 11/2010 | Ryu | |
| 2006/0084830 A1 | 4/2006 | Ryu | |

FOREIGN PATENT DOCUMENTS

| | | |
|---|---|---|
| CN | 1087892 | 6/1994 |
| CN | 1280975 A | 1/2001 |
| CN | 1298376 A | 6/2001 |
| CN | 1852877 | 10/2006 |
| CN | 1852877 A | 10/2006 |
| CN | 101121633 A | 2/2008 |
| CN | 101432247 A | 5/2009 |
| CN | 101475438 A | 7/2009 |
| CN | 101475439 | 7/2009 |
| JP | 59-216838 | 12/1984 |
| JP | 63-291643 | 11/1988 |
| JP | 03-204825 | 9/1991 |
| JP | 06-157362 | 6/1994 |
| JP | 2001-269580 | 10/2001 |

OTHER PUBLICATIONS

Jackson et al. Applied Catalysis A: General 134 (1996) 91-99.*
Molnar et al. Hydrogenation of Carbon-Carbon Multiple Bonds: Chemo-, Regio-, and Stereo-Selectivity. Journal of Molecular Catalysis A: Chemical 173 (2001) 185-221.*
International Search Report from the Chinese Patent Office in International Application No. PCT/CN2009/001486 mailed Mar. 25, 2010.
International Search Report from the Chinese Patent Office for International Patent Application No. PCT/CN2009/001487, mailed Mar. 25, 2010.
Copending U.S. Appl. No. 13/140,645, filed Jun. 17, 2011.

* cited by examiner

*Primary Examiner* — In Suk Bullock
*Assistant Examiner* — Sharon Pregler
(74) *Attorney, Agent, or Firm* — Finnegan, Henderson, Farabow, Garrett & Dunner LLP

(57) ABSTRACT

The present invention discloses a process for the selective hydrogenation of phenylacetylene in the presence of styrene, comprising contacting a phenylacetylene and styrene-containing hydrocarbon fraction feedstock with a carbon-containing catalyst under hydrogenation reaction conditions, wherein the carbon-containing catalyst has a carbon content of from 0.02 to 8 wt % based on the weight of the catalyst.

10 Claims, No Drawings

US 9,084,984 B2

METHOD FOR SELECTIVE HYDROGENATION OF PHENYLACETYLENE IN THE PRESENCE OF STYRENE

CROSS REFERENCE OF RELATED APPLICATION

The present application claims the priority of Application No. CN200810044146.0 filed on Dec. 18, 2008, which is incorporated herein by reference in its entirety and for all purposes.

FIELD OF THE INVENTION

The present invention relates to a process for the selective hydrogenation of phenylacetylene in the presence of styrene, in particular to a process for removing phenylacetylene from a phenylacetylene-containing $C_8$ hydrocarbon fraction feedstock.

BACKGROUND ART

Styrene (ST) is an important monomer for producing polystyrene (PS), ABS resin, styrene-butadiene rubber, etc., and it is mainly produced by a process of dehydrogenating ethylbenzene. In recent years, along with the development and scale-up of ethylene industry, the technology of recovering styrene from pyrolysis gasoline draws more and more attention.

Pyrolysis gasoline is a by-product of ethylene industry, of which output is about 60 to 70% of ethylene output. $C_8$ fraction of pyrolysis gasoline is rich in styrene and mixed xylenes. An ethylene plant in 1000 kt/a scale can produce 24 to 42 kt/a of styrene, and at the same time mixed xylenes can be recovered. The production cost of styrene recovered from pyrolysis gasoline is about ½ of that of styrene produced by a process of dehydrogenating ethylbenzene.

The process for recovering styrene from pyrolysis gasoline that is widely regarded as being feasible at present is an extraction-distillation process. However, phenylacetylene (PA) and styrene are similar in chemical structure, and they also have similar interaction with an extraction-distillation solvent, so that it is impossible to achieve an effective separation of styrene from PA by the extraction-distillation. The presence of PA will not only increase the consumption of catalyst during anionic polymerization of styrene and affect chain length and polymerization rate, but also lead to worsen properties of polystyrene, e.g., off-color, degradation, odor-releasing and the like. Therefore, it is necessary to remove phenylacetylene from a styrene stream, while the loss of styrene should be as low as possible. Accordingly, the development of a high selectivity catalyst for the selective hydrogenation of phenylacetylene and of a relevant process becomes a key of the technology of recovering styrene from pyrolysis gasoline.

Patent application CN1852877A discloses a process for the reduction of phenylacetylene impurity in the presence of styrene monomer. A styrene monomer stream containing a minor amount of phenylacetylene is supplied to a hydrogenation reactor, and a hydrogenation gas comprising hydrogen is also supplied to the hydrogenation reactor. The styrene monomer stream and the hydrogen are brought into contact with a catalyst bed containing a catalyst comprising a reduced copper compound on a θ-alumina support. The hydrogenation reactor is operated at a temperature of at least 60° C. and a pressure of at least 30 psig to hydrogenate phenylacetylene to styrene. The hydrogenation gas comprises a mixture of nitrogen and hydrogen. This technique is featured with a relatively high reaction temperature, a low hydrogenation rate of phenylacetylene (about 70%), a short lifetime of catalyst, and a high loss of styrene (about 3%).

Patent application CN1087892A discloses a process and apparatus for purifying styrene monomer in a styrene stream by hydrogenation, wherein a diluent such as nitrogen is used to dilute hydrogen, the hydrogen is supplied by a vent gas from the dehydrogenation of ethylbenzene, and phenylacetylene impurity is hydrogenated to styrene by the aid of a multi-stage catalyst bed reactor. This patent is only directed to a process for the selective removal of phenylacetylene from a styrene stream containing phenylacetylene at a low concentration such as 300 ppm. On the other hand, the catalyst used exhibits a low hydrogenation rate of phenylacetylene (about 95%), and the loss of styrene is about 0.2%.

Thus, there is still need for a process to selectively hydrogenate phenylacetylene with a high selectivity useful in the technology for recovering styrene from pyrolysis gasoline.

SUMMARY OF THE INVENTION

In order to overcome the problems that the removal rate of phenylacetylene is low and that the loss of styrene is high, suffered by the existing techniques for removing phenylacetylene from a styrene stream by hydrogenation, the inventors have made diligently studies. As a result, the inventors have found that by using a hydrogenation catalyst containing a certain amount of carbon, phenylacetylene in a styrene stream can be effectively removed and, at the same time, the loss of styrene is very low. On this basis, the present invention has been made.

Thus, an object of the present invention is to provide a novel process for the selective hydrogenation of phenylacetylene in the presence of styrene, comprising contacting a phenylacetylene and styrene-containing hydrocarbon fraction feedstock with a carbon-containing catalyst under hydrogenation reaction conditions, wherein the carbon-containing catalyst has a carbon content of from 0.02 to 8 wt % based on the weight of the catalyst. The process has advantages that the removal rate of phenylacetylene is high and that the loss of styrene is low.

DESCRIPTION OF PREFERRED EMBODIMENTS

In an embodiment, the present invention relates to a process for the selective hydrogenation of phenylacetylene in the presence of styrene, comprising contacting a phenylacetylene and styrene-containing hydrocarbon fraction feedstock with a carbon-containing catalyst under hydrogenation reaction conditions, wherein the carbon-containing catalyst has a carbon content of from 0.02 to 8 wt % based on the weight of the catalyst.

In a preferred embodiment, the hydrogenation reaction conditions include: a reaction temperature of from 15 to 100° C., and preferably from 25 to 60° C.; a weight hourly space velocity of from 0.01 to 100 $hr^{-1}$, and preferably from 0.1 to 20 $hr^{-1}$; a molar ratio of hydrogen/phenylacetylene of from 1:1 to 30:1, and preferably from 1:1 to 10:1; and a reaction pressure of from −0.08 to 5.0 MPa (gauge, the same below), and preferably from 0.1 to 3.0 MPa.

The carbon-containing catalyst used in the process of the present invention contains nickel and/or palladium as active ingredient. In an embodiment, the catalyst contains nickel, with a nickel content ranging from 10 to 50 wt % based on the weight of the support. In another embodiment, the catalyst contains palladium, with a palladium content ranging from 0.1 to 3 wt % based on the weight of the support. The support of the catalyst is at least one selected from the group consisting of silica, magnesia, alumina and molecular sieves, and preferably at least one of silica and alumina. The catalyst has a carbon content of from 0.02 to 8 wt %, preferably from 0.03 to 5 wt %, and more preferably from 0.05 to 3 wt %, based on the weight of the catalyst.

The carbon-containing catalysts may be prepared by processes known per se. For example, a carbon-containing nickel-based catalyst may be prepared by a process comprising the steps of: adding slowly an amount of a water-soluble nickel salt, e.g., nickel nitrate, into an aqueous diluted acid (e.g., nitric acid) solution and stirring to dissolve the nickel salt; impregnating an amount of a support, e.g., alumina, with the resulting solution for, for example, more than 8 hours; then drying and calcining the impregnated support, followed by a hydrogen reduction, to obtain a nickel-based catalyst; then subjecting the nickel-based catalyst to a carbon pre-deposition treatment using styrene at, for example, 100° C. under ambient pressure, to obtain a carbon-containing nickel-based catalyst having a desired carbon deposit amount. For another example, a carbon-containing palladium-based catalyst may be prepared by a process comprising the steps of: pre-impregnating an amount of a support, e.g., alumina, with deionized water, and then filtering off the water; dissolving an amount of a water-soluble palladium salt, e.g., palladium nitrate, in water, and adjusting the solution with nitric acid to a pH value of about 3 to about 6; after suitably heating the solution, impregnating the water-filtered-off support with the solution; drying the impregnated support and calcining it in air, followed by a hydrogen reduction, to obtain a palladium-based catalyst; then subjecting the palladium-based catalyst to a carbon pre-deposition treatment using styrene at, for example, 100° C. under ambient pressure, to obtain a carbon-containing palladium-based catalyst having a desired carbon deposit amount.

The process of the present invention can be used for removing phenylacetylene from a styrene-containing stream. There is not a specific limitation to the feedstock used in the process of the present invention, as long as it contains styrene and phenylacetylene. The feedstock used in the process of the present invention may be a $C_8$ fraction recovered from pyrolysis gasoline. Such a fraction may contain 20 to 60 wt % of styrene and 0.03 to 2 wt % of phenylacetylene.

It is well known that the hydrogenation reaction of phenylacetylene is a typical tandem reaction. Phenylacetylene is firstly hydrogenated to form styrene, and then the styrene may be further hydrogenated to form ethylbenzene. Ethylbenzene has an added value far lower than that of styrene, and thus the hydrogenation of styrene is undesired. Meanwhile, the presence of phenylacetylene is disadvantageous to subsequent separation, and affects the reaction of styrene, so that it is desired to remove phenylacetylene as much as possible. Therefore, furthest converting phenylacetylene whilst furthest avoiding the loss of styrene by hydrogenation is crucial for the technology of recovering styrene. After a lot of studies, we have discovered that, in the process of hydrogenating phenylacetylene with a palladium- or nickel-based catalyst, the reaction activation energy of the step of hydrogenating phenylacetylene to produce styrene is far lower than that of the step of hydrogenating styrene to produce ethylbenzene, so that both the palladium-based catalyst and the nickel-based catalyst have a relatively good selectivity for the hydrogenation of phenylacetylene. In addition, after further studies, the inventors have surprisingly discovered that the palladium-based or nickel-based catalyst, after modified with a certain amount of carbon deposits, exhibits a better selectivity for the hydrogenation of phenylacetylene. By using a palladium-based or nickel-based catalyst having subjected to the treatment of pre-depositing carbon, the present process can maximize the conversion of phenylacetylene and, at the same time, furthest avoid the loss of styrene by hydrogenation. The present process exhibits especially an even more prominent advantage at the initial stage of running.

In one embodiment of the invention, a $C_8$ fraction feedstock containing 20 to 60 wt % of styrene and 0.03 to 2 wt % of phenylacetylene is brought into contact with a catalyst containing alumina as a support, nickel as an active ingredient, and 0.08 to 5 wt % of carbon under the conditions of a reaction temperature of 25 to 60° C., a weight hourly space velocity of 0.1 to 20 $hr^{-1}$, a molar ratio of hydrogen/phenylacetylene of 1:1 to 20:1, and a reaction pressure of 0.1 to 3.0 MPa, to fulfill the selective hydrogenation of phenylacetylene. Under such conditions, the hydrogenation rate of phenylacetylene may be up to 100%, while the loss of styrene may be zero, and even the situation where the amount of styrene is increased (or the loss of styrene is negative) due to the hydrogenation of phenylacetylene into styrene may occur.

EXAMPLES

The following examples are given for further illustrating the invention, but do not make limitation to the invention in any way.

Example 1

By using θ-alumina as support, 10 g nickel-based catalyst precursor having a nickel loading amount of 13 wt % was prepared by a supporting process. The catalyst precursor was activated with hydrogen at 400° C. for 4 hrs, to obtain a nickel-based catalyst. The nickel-based catalyst was subjected to carbon pre-deposition treatment using styrene at 100° C. under ambient pressure for 4 hrs, to obtain a nickel-based catalyst having a carbon deposit amount of 0.08 wt % based on the catalyst. A $C_8$ fraction feedstock containing 40 wt % of styrene, 10 wt % of ethylbenzene, and 0.1 wt % of phenylacetylene was brought into contact with the carbon pre-deposited catalyst in a fixed-bed reactor under the following conditions: a reaction temperature of 40° C., a weight hourly space velocity of 2 $hr^{-1}$, a molar ratio of hydrogen/phenylacetylene of 3:1, and a reaction pressure of 0.5 MPa. By analyzing the effluent from the reactor, it was found that the loss of styrene was 0.1 wt %, and the content of phenylacetylene was 1 ppmw.

Example 2

By using θ-alumina as support, 10 g nickel-based catalyst precursor having a nickel loading amount of 45 wt % was prepared by a supporting process. The catalyst precursor was activated with hydrogen at 400° C. for 4 hrs, and then was subjected to carbon pre-deposition treatment according to the procedure described in Example 1, to obtain a carbon pre-deposited nickel-based catalyst having a carbon deposit amount of 1 wt % based on the catalyst. A $C_8$ fraction feedstock containing 35 wt % of styrene, 12 wt % of ethylbenzene, and 0.2 wt % of phenylacetylene was brought into contact with the carbon pre-deposited catalyst in a fixed-bed reactor under the following conditions: a reaction temperature of 35° C., a weight hourly space velocity of 0.2 $hr^{-1}$, a molar ratio of hydrogen/phenylacetylene of 10:1, and a reaction pressure of 2.5 MPa. By analyzing the effluent from the reactor, it was found that the loss of styrene was 0, and phenylacetylene was undetectable.

Example 3

By using γ-alumina as support, 10 g nickel-based catalyst precursor having a nickel loading amount of 20 wt % was prepared by a supporting process. The catalyst precursor was activated with hydrogen at 400° C. for 4 hrs, and then was subjected to carbon pre-deposition treatment according to the procedure described in Example 1, to obtain a carbon pre-deposited nickel-based catalyst having a carbon deposit amount of 3 wt % based on the catalyst. A $C_8$ fraction feedstock containing 20 wt % of styrene, 15 wt % of ethylbenzene, and 0.06 wt % of phenylacetylene was brought into contact with the carbon pre-deposited catalyst in a fixed-bed reactor under the following conditions: a reaction temperature of 70° C., a weight hourly space velocity of 20 $hr^{-1}$, a molar ratio of hydrogen/phenylacetylene of 3:1, and a reaction pressure of 0.5 MPa. By analyzing the effluent from the reactor, it was found that the loss of styrene was 0.1 wt %, and the content of phenylacetylene in the effluent was 5 ppmw.

Example 4

By using ZSM-5 molecular sieve as support, 10 g nickel-based catalyst precursor having a nickel loading amount of 30 wt % was prepared by a supporting process. The catalyst precursor was activated with hydrogen at 400° C. for 4 hrs, and then was subjected to carbon pre-deposition treatment according to the procedure described in Example 1, to obtain a carbon pre-deposited nickel-based catalyst having a carbon deposit amount of 0.05 wt % based on the catalyst. A $C_8$ fraction feedstock containing 34 wt % of styrene, 8 wt % of ethylbenzene, and 1.2 wt % of phenylacetylene was brought into contact with the carbon pre-deposited catalyst in a fixed-bed reactor under the following conditions: a reaction temperature of 45° C., a weight hourly space velocity of 3 $hr^{-1}$, a molar ratio of hydrogen/phenylacetylene of 30:1, and a reaction pressure of 1.5 MPa. By analyzing the effluent from the reactor, it was found that the loss of styrene was −0.5 wt %, and phenylacetylene was undetectable.

Example 5

By using a 1:1 by weight mixture of γ- and α-alumina as support, 10 g nickel-based catalyst precursor having a nickel loading amount of 25 wt % was prepared by a supporting process. The catalyst precursor was activated with hydrogen at 400° C. for 4 hrs, and then was subjected to carbon pre-deposition treatment according to the procedure described in Example 1,to obtain a carbon pre-deposited nickel-based catalyst having a carbon deposit amount of 0.2 wt % based on the catalyst. A $C_8$ fraction feedstock containing 56 wt % of styrene, 5 wt % of ethylbenzene, and 2 wt % of phenylacetylene was brought into contact with the carbon pre-deposited catalyst in a fixed-bed reactor under the following conditions: a reaction temperature of 80° C., a weight hourly space velocity of 8 $hr^{-1}$, a molar ratio of hydrogen/phenylacetylene of 4:1, and a reaction pressure of 0.6 MPa. By analyzing the effluent from the reactor, it was found that the loss of styrene was −1 wt %, and the content of phenylacetylene in the effluent was 3 ppmw.

Example 6

By using γ-alumina as support, 10 g palladium-based catalyst precursor having a palladium loading amount of 0.5 wt % was prepared by a supporting process. The catalyst precursor was activated with hydrogen at 350° C. for 4 hrs, and then was subjected to carbon pre-deposition treatment according to the procedure described in Example 1, to obtain a carbon pre-deposited palladium-based catalyst having a carbon deposit amount of 1.2 wt % based on the catalyst. A $C_8$ fraction feedstock containing 26 wt % of styrene, 8 wt % of ethylbenzene, and 0.06 wt % of phenylacetylene was brought into contact with the carbon pre-deposited catalyst in a fixed-bed reactor under the following conditions: a reaction temperature of 60° C., a weight hourly space velocity of 3 $hr^{-1}$, a molar ratio of hydrogen/phenylacetylene of 10:1, and a reaction pressure of 1.5 MPa. By analyzing the effluent from the reactor, it was found that the loss of styrene was 0.5 wt %, and the content of phenylacetylene in the effluent was 10 ppmw.

Example 7

By using γ-alumina as support, 10 g palladium-based catalyst precursor having a palladium loading amount of 3 wt % was prepared by a supporting process. The catalyst precursor was activated with hydrogen at 350° C. for 4 hrs, and then was subjected to carbon pre-deposition treatment according to the procedure described in Example 1, to obtain a carbon pre-deposited palladium-based catalyst having a carbon deposit amount of 3 wt % based on the catalyst. A $C_8$ fraction feedstock containing 36 wt % of styrene, 5 wt % of ethylbenzene, and 0.08 wt % of phenylacetylene was brought into contact with the carbon pre-deposited catalyst in a fixed-bed reactor under the following conditions: a reaction temperature of 65° C., a weight hourly space velocity of 5 $hr^{-1}$, a molar ratio of hydrogen/phenylacetylene of 20:1, and a reaction pressure of −0.05 MPa. By analyzing the effluent from the reactor, it was found that the loss of styrene was 0.05 wt %, and phenylacetylene was undetectable.

Comparative Example 1

The experiment was carried out according to the procedure described in Example 1, except that the catalyst was not subjected to carbon pre-deposition treatment. By analyzing the effluent from the reactor, it was found that the loss of styrene was 5 wt %, and the content of phenylacetylene in the effluent was 0.5 ppmw.

Comparative Example 2

The experiment was carried out according to the procedure described in Example 6, except that the catalyst was not subjected to carbon pre-deposition treatment. By analyzing the effluent from the reactor, it was found that the loss of styrene was 8 wt %, and phenylacetylene was undetectable.

The patents, patent applications and testing methods cited in the specification are incorporated herein by reference.

While the invention has been described with reference to exemplary embodiments, it will be understood by those skilled in the art that various changes and modifications may be made without departing from the spirit and scope of the invention. Therefore, the invention is not limited to the particular embodiments disclosed as the best mode contemplated for carrying out this invention, but the invention will include all embodiments falling within the scope of the appended claims.

What is claimed is:
1. A process for the selective hydrogenation of phenylacetylene in the presence of styrene, comprising contacting a phenylacetylene and styrene-containing hydrocarbon frac- tion feedstock with a carbon pre-deposited catalyst under hydrogenation reaction conditions, wherein the carbon pre-deposited catalyst has a carbon content of from 0.02 to 8 wt % based on the weight of the catalyst.

2. The process according to claim 1, wherein the hydrogenation reaction conditions include: a reaction temperature of from 15 to 100° C., a weight hourly space velocity of from 0.01 to 100 $hr^{-1}$, a molar ratio of hydrogen/phenylacetylene of from 1:1 to 30:1, and a reaction pressure of from −0.08 to 5.0 MPa.

3. The process according to claim 1, wherein the carbon pre-deposited catalyst has a carbon amount of from 0.03 to 5 wt % based on the weight of the catalyst.

4. The process according to claim 1, wherein the carbon pre-deposited catalyst has a carbon amount of from 0.05 to 3 wt % based on the weight of the catalyst.

5. The process according to claim 1, wherein the p carbon pre-deposited catalyst contains nickel and/or palladium as active ingredient, and at least one selected from the group consisting of silica, magnesia, alumina and molecular sieves as support.

6. The process according to claim 5, wherein the carbon pre-deposited catalyst contains nickel as active ingredient, and the content of nickel ranges from 10 to 50 wt % based on the weight of support.

7. The process according to claim 5, wherein the carbon pre-deposited catalyst contains palladium as active ingredient, and the content of palladium ranges from 0.1 to 3 wt % based on the weight of support.

8. The process according to claim 1, wherein the hydrogenation reaction conditions include: a reaction temperature of from 25 to 60° C., a weight hourly space velocity of from 0.1 to 20 $hr^{-1}$, a molar ratio of hydrogen/phenylacetylene of from 1:1 to 20:1, and a reaction pressure of from 0.1 to 3.0 MPa.

9. The process according to claim 1, wherein the phenylacetylene and styrene-containing hydrocarbon fraction feedstock contains 20 to 60 wt % of styrene and 0.03 to 2 wt % of phenylacetylene.

10. The process according to claim 1, wherein the phenylacetylene and styrene-containing hydrocarbon fraction feedstock is a $C_8$ fraction recovered from pyrolysis gasoline.

* * * * *